United States Patent
Sudo et al.

[11] Patent Number: 6,090,081
[45] Date of Patent: Jul. 18, 2000

[54] SEALING STOPPER FOR A SYRINGE AND A PREFILLED SYRINGE

[75] Inventors: Masamichi Sudo; Tomoyasu Muraki, both of Tokyo, Japan

[73] Assignee: Daikyo Seiko, Ltd., Tokyo, Japan

[21] Appl. No.: 09/081,644

[22] Filed: May 20, 1998

[30] Foreign Application Priority Data

May 22, 1997 [JP] Japan .................................... 9-132297

[51] Int. Cl.[7] .................................................. A61M 5/315
[52] U.S. Cl. ............................................ 604/230; 604/218
[58] Field of Search .................................. 604/230, 218, 604/187

[56] References Cited

U.S. PATENT DOCUMENTS

| | | |
|---|---|---|
| 4,554,125 | 11/1985 | Knapp . |
| 4,633,765 | 1/1987 | Knodel ..................................... 604/230 |
| 4,997,423 | 3/1991 | Okuda et al. . |
| 5,194,335 | 3/1993 | Effenberger et al. . |
| 5,527,580 | 6/1996 | Ikeda et al. . |
| 5,639,851 | 6/1997 | Bezwada et al. .................... 604/230 X |
| 5,951,527 | 9/1999 | Sudo ....................................... 604/218 |

FOREIGN PATENT DOCUMENTS

| | | |
|---|---|---|
| 0 338 671 | 10/1989 | European Pat. Off. . |
| 0 528 529 | 2/1993 | European Pat. Off. . |
| 0 743 072 | 11/1996 | European Pat. Off. . |
| 48-8990 | 1/1973 | Japan . |
| 62-139668 | 6/1987 | Japan . |
| 63-97173 | 4/1988 | Japan . |
| 1-138454 | 9/1989 | Japan . |
| 1-138455 | 9/1989 | Japan . |
| 5-293159 | 9/1993 | Japan . |

OTHER PUBLICATIONS

Cf. "Plastic No Jiten (Plastic Dictionary)", pp. 836–838, published by Asakura Shoten, Mar. 1, 1992.
Japanese Pharmacopoeia Thirteenth Edition, pp. 9–27.

*Primary Examiner*—John D. Yasko
*Attorney, Agent, or Firm*—Wenderoth, Lind & Ponack, L.L.P.

[57] ABSTRACT

There can be provided a sealing stopper for a syringe, having very high sealing property and sliding property, and a prefilled syringe using this sealing stopper and capable of preserving a medicament for a long time and operating in easy and precise manner during injecting. This syringe is also excellent in sanitary and operating property during a step of formulation or preservation of a medicament. In this sealing stopper for a syringe, a surface of the rubber body is laminated with a tetrafluoroethylene resin film or ultra-high molecular weight polyethylene film having an average roughness Ra on the central line of the surface in a range of at most 0.05 $\mu$m and a kinematic friction coefficient of at most 0.2.

4 Claims, 3 Drawing Sheets

SEALING STOPPER FOR A SYRINGE AND A PREFILLED SYRINGE

BACKGROUND OF THE INVENTION

1. Field of the Invention

This invention relates to a sealing stopper for a syringe and a prefilled syringe consisting of an injection cylinder or two-component cylinder in which a medicament is sealed by the use of the sealing stopper for a syringe.

2. Description of the Prior Art

An injection agent as one agent form of a medicament includes a solid formulation to be dissolved in administering and a liquid formulation prepared in the form of a solution. As a means for administering an injection agent in the body, there are a method comprising directly administering a medicament liquid in the body from a syringe and a method comprising mixing an injection agent with another medicament liquid held by another container just before administering and then introducing the mixture into the body through an administering system, for example, another medical instrument than syringes, such as drip injection set.

In the so-called prefilled syringe, an injection agent is previously filled in an injection cylinder-cum-container, transported or kept in custody, while sealing the end thereof by a sealing stopper. For the adminisration of the injection agent, an injection needle or administration device is fitted to the pointed end, after which the sealing stopper is thrust toward the pointed end and slidably moved to allow the injection agent to flow out of the injection needle side and administer it. This syringe of prefilled type has various advantages that ① operation thereof is very simple, ② administration of a medicament is feasible with a correct administration quantity without misuse of a medicament even in case of emergency and ③ removal of a medicament is not required to prevent the medicament from contamination with microorganisms and to maintain highly sanitary conditions. Thus, the syringe of prefilled type has lately been used often so as to improve the efficiency of medical treatment in the actual medical scene and to prevent contamination with microorganisms. Further, it has been recommended to use a so-called kit article consisting of a system of a solid agent, water for dissolving the solid agent and a medicament liquid, in combination, because of the same reason.

Such a prefilled syringe is convenient as described above, but when a medicament is kept in custody, high sealing property is required and simultaneously, slidable movement of a sealing stopper is required in administering. Namely, the prefilled syringe must have a function of opposite properties, that is, sealing property and slidable property.

In syringes of the prior art, silicone oils have been coated onto a piston to unite both the sealing property and slidable property. Of late, however, there arise problems, for example, lowering of the potency due to adsorption of effective components of a medicament on the silicone oil, contamination of a medicament with fine grains as a stripped product of a silicone oil and bad influences upon the human body thereby (poisonous character of silicone oil). Accordingly, there is a late tendency of avoiding use of silicone oils.

On the other hand, a movable sealing rubber stopper (which will hereinafter be referred to as "sealing stopper" in some cases) whose main body consists of a rubber has hitherto been known. Examples include one having a fluoro resin film such as tetrafluoroethylene laminated on the surface to be contacted with a medicament liquid (Japanese Utility Model Publication No. 8990/1973), a sealing rubber stopper for and a prefilled syringe having a polypropylene resin film laminated on all sites to be contacted with an inner surface of a syringe (U.S. Pat. No. 4,554,125), etc.

Under the situation, the inventors have developed and proposed syringes or two-component syringes capable of satisfying both the sealing property and slidable property without using silicone oils and having high sanitary and safety property. Examples include a sealing stopper whose surface is coated with a tetrafluoroethylene-ethylene copolymer resin (which will hereinafter be referred to as "ETFE" in some cases), as disclosed in Japanese Patent Laid-Open Publication No. 139668/1987, a sealing stopper whose surface is coated with a polytetrafluoroethylene resin film (which will hereinafter be referred to as "PTFE" in some cases), as disclosed in Japanese Patent Laid-Open Publication No. 97173/1988, and a sealing stopper laminated with PTFE, ETFE or ultrahigh molecular polyethylene resin film having a shape suitable for a prefilled syringe, as disclosed in Japanese Utility Model Laid-Open Publication No. 138454/1989 or 138455/1989. Furthermore, there has been proposed a syringe consisting of a cyclic olefin plastic capable of satisfying both the sealing property and slidable property in combination with the sealing stopper as described above, as disclosed in Japanese Patent Laid-Open Publication No. 293159/1993.

In the general formulation provisions of the Japanese Pharmacopoeia of 13th Revision, it is provided that a container for an injection agent must be a hermetic container and the hermetic container is defined as a container capable of daily handling and preventing a medicament from being contaminated with gases or microorganisms during ordinary storage. Considering the prior art in view of this official provision, the resin film-laminated sealing stopper has a large effect on inhibition of dissolving-out of a rubber component of the stopper body, but the sealing property tends to be lowered because of not using silicone oil.

In the above described sealing stopper the inventors have developed, it is necessary in order to maintain a sufficient-sealing property to design so that a difference between the outer diameter of the sealing stopper and the inner diameter of the syringe is somewhat large. Consequently, there arises a problem that the sliding resistance during administering a medicament is somewhat increased.

On the other hand, the inventors have made various studies about resins to be laminated on surfaces of sealing stoppers and consequently, have reached a conclusion that PTFE is most suitable, and that high molecular weight polyethylene (which will hereinafter be referred to as "UHMWPE" some times) is preferably used in addition to fluoro resins, as compared with other fluoro resins. Examples include tetrafluoroethylene-perfluoroethylenc copolymer (PFA), tetrafluoroethylenene-hexafluoropropylene copolymer (FEP), tetrafluoroethylene-ethylene copolymer (ETFE), trichlorotrifluoroethylene (PCTFE), polyvinylidene fluoride (PVDF), polyvinyl fluoride (PVF), etc. The reasons therefor will be illustrated below.

The above described other fluoro resins can be subjected to thermal melt molding, for example, injection molding or extrusion molding, but PTFE having a melt flow rate (MFR) of substantially zero at its melting point of 327° C. and being non-sticky cannot be subjected to thermal melt molding [Cf. "Plastic No Jiten (Plastic Dictionary)", page 836–838, published by Asakura Shoten, Mar. 1, 1992]. Accordingly, a film of PTFE is obtained by compression molding to give a sheet, by shaping in a block and cutting or slicing the block to give a relatively thick sheet or by skiving working to give a thinner film.

The skiving method will further be illustrated in detail. A suitable amount of a powdered resin raw material for shaping working, obtained by suspension polymerization to give a grain diameter of ~10 µm, is charged in a metallic mold for sintering shaping, previously shaped at room temperature and at a pressure of 100 to 1000 kg/cm² in a compression press and then sintered at 360 to 380° C. for several hours ordinarily but depending on the size of a shaped product. Then, the metallic mold is cooled at normal pressure or at some pressure, thus obtaining a primary shaped product in the form of a sheet, block or cylinder. The shaped product of PTFE in the form of a cylinder, obtained in the above described compression shaping, is fitted to a lathe and revolved, during which an edged tool is pressed against the shaped product at a constant pressure and a specified angle to obtain a PTFE film with a thickness of 40 to 50 µm and at most 200 µm.

The film prepared by this skiving method has a disadvantage that there remain pinholes or skiving scratches on the surface thereof and accordingly, the film is not suitable for laminating a sealing stopper for preventing it from leaching of rubber components in a medicament and contaminating the medicament.

On the other hand, a casting method comprising adding a latex emulsion to a suspension of fine grains of a fluoro resin, thinly spreading the mixture on a metallic surface and then burning to obtain a film has been known as disclosed in U.S. Pat. No. 5,194,335. According to this method, a film with a thickness of up to about 3 µm can be produced.

SUMMARY OF THE INVENTION

It is an object of the present invention to provide a sealing stopper for a syringe and a prefilled syringe, whereby the above described problems can he resolved.

It is another object of the present invention to provide a sealing rubber stopper for a syringe, in which a surface of the rubber body is laminated with a PTFE film or UHMWPE film, whereby more sufficient and excellent sealing property and slidable property as compared with those of the prior art can be given without using silicone oil.

It is a further object of the present invention to provide a sealing rubber stopper for a syringe, in which a surface of the rubber body is laminated with a PTFE film or UHMWPE film, having no pinholes nor scratches and having high sanitary property.

It is a still further object of the present invention to provide a prefilled syringe, in which a medicament is enclosed and sealed in an injection cylinder or two-component cylinder by the use of the sealing stopper for a syringe.

These objects can be attained by a sealing stopper for a syringe, in which a surface of the rubber body is laminated with a tetrafluoroethylene resin film or ultra-high molecular weight polyethylene film having an average roughness Ra on the central line of the surface in a range of at most 0.05 µm and a kinematic friction coefficient of at most 0.2, and a prefilled syringe, in which a medicament is enclosed and sealed in an injection cylinder or two-component cylinder by the use of the sealing stopper for a syringe. A surface of tie rubber body is laminated with a tetrafluoroethylene resin film or ultra-high molecular weight polyethylene film having an average roughness Ra on the central line of the surface in a range of at most 0.05 µm and a kinematic friction coefficient of at most 0.2.

BRIEF DESCRIPTION OF THE DRAWINGS

The accompanying drawings are to illustrate the principle and merits of the present invention in detail.

DETAILED DESCRIPTION OF THE INVENTION

The inventors have made various studies to develop a sealing stopper laminated with a PTFE film or UHMWPE film capable of preventing the rubber body from elution of rubber components and contamination of a medicament in contact with the rubber stopper. Accordingly, it is found that the PTFE film or UHMWPE film having the specified surface roughness and kinematic friction coefficient is effective for this purpose.

As a means for solving the above described problems, there are provided the following inventions and embodiments:

(1) A sealing stopper for a syringe, in which a surface of the rubber body is laminated with a tetrafluoroethylene resin film or ultra-high molecular weight polyethylene film having an average roughness Ra on the central line of the surface in a range of at most 0.05 µm and a kinematic friction coefficient of at most 0.2.

(2) The sealing stopper for a syringe, as described in the above (1), wherein the tetrafluoroethylene resin film is prepared by a casting shaping method comprising using, as a raw material, a suspension containing tetrafluoroethylene resin powder having a grain diameter of at most 0.01 to 1.0 µm, a dispersing agent and a solvent.

(3) The sealing stopper for a syringe, as described in the above (1), wherein the ultra-high molecular weight polyethylene film is prepared by an inflation shaping method or extrusion shaping method.

(4) A prefilled syringe, in which a medicament is enclosed and sealed in an injection cylinder or two-component cylinder by the use of the sealing stopper for a syringe. A surface of the rubber body is laminated with a tetrafluoroethylene resin film or ultrahigh molecular weight polyethylene film having an average roughness Ra on the central line of the surface in a range of at most 0.05 µm and a kinematic friction coefficient of at most 0.2.

(5) A process for the production of a sealing stopper for a syringe, which comprises preparing a suspension of polytetrafluoroethylene fine grains having a maximum grain diameter in a range of 0.01 to 1.0 µm with a concentration of 40 to 50% in a suitable solvent containing a dispersing agent, coating the resulting suspension onto a metallic belt, and heating and drying the coating at a temperature of higher than the melting point of polytetrafluoroethylene to form a thin film. This procedure is to obtain a sintered cast film with a suitable thickness and then laminating a rubber body with the cast film.

(6) The process for the production of a sealing stopper for a syringe, as described in the above (5), wherein the thin film has a thickness of 5 to 20 µm and the sintered cast film has a thickness of 10 to 60 µm.

Figure 1:
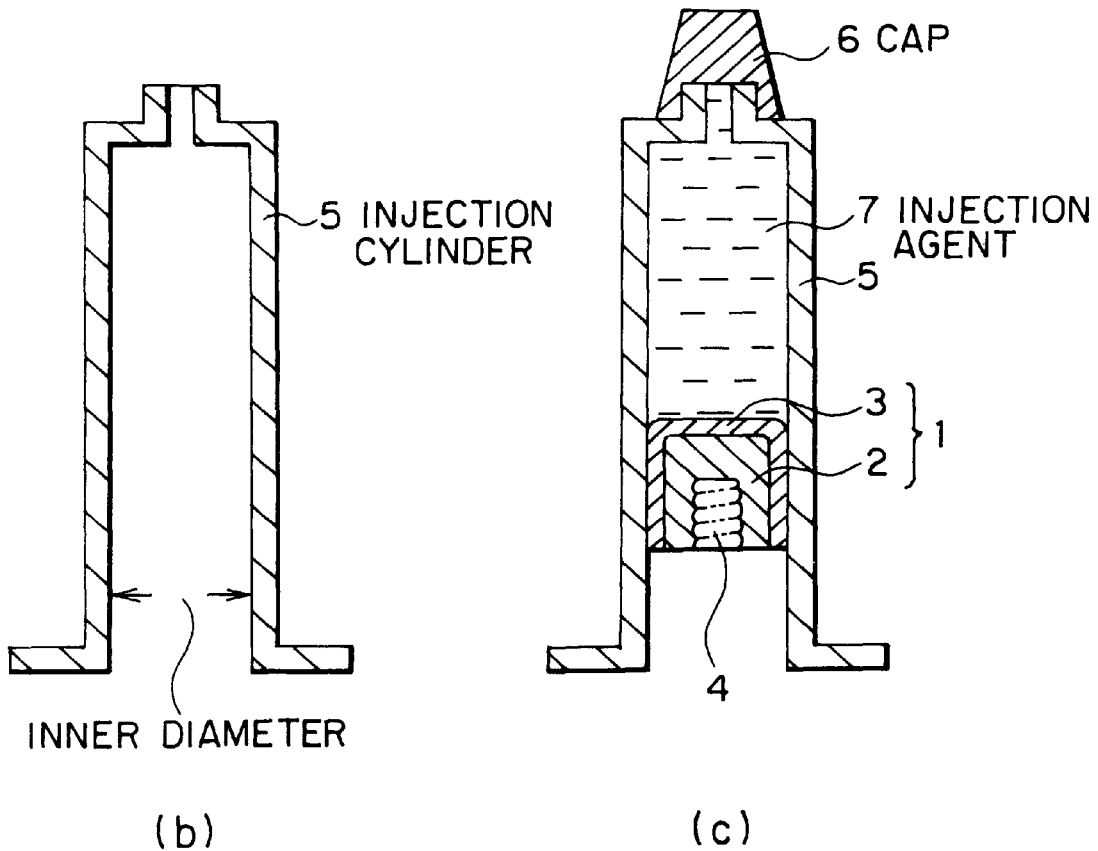
FIG. 1(a), (b) and (c) are cross-sectional views of structures of a sealing stopper and prefilled syringe according to the present invention.
Figure 1:
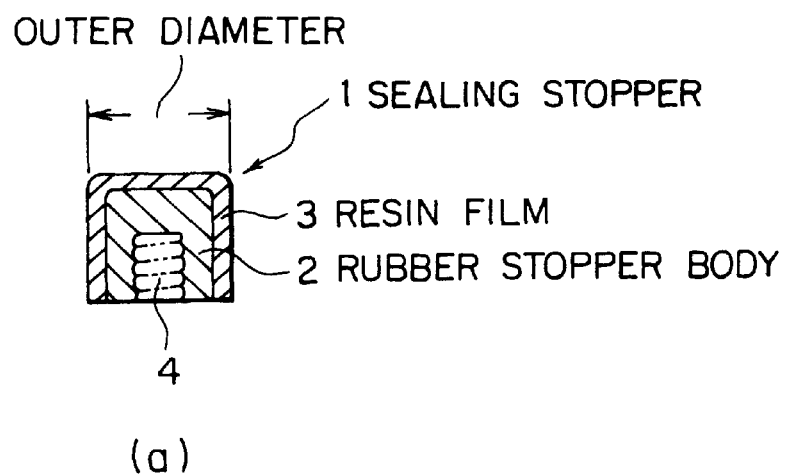

Referring to FIG. 1 showing a sealing stopper for a syringe (which will hereinafter be referred to as "sealing stopper") and a prefilled syringe of the present invention, a sealing stopper 1 shown in FIG. 1(a) comprises a rubber stopper body 2 whose surface is laminated with a resin film 3. 4 designates a fitting part of a plunger not shown. In a formulation step for an injection medicament, the end of an injection cylinder 5 shown in FIG. 1 (b) is sealed by a cap 6, and an injection medicament 7 is charged for the formulation in an injection cylinder 5, followed by sealing by the sealing stopper 1 to prepare a prefilled syringe. Ordinarily, an injection needle, plunger and covers for the various parts (not shown) are adapted to the prefilled syringe, thus obtaining a finished product.

The inventors have made various studies and investigations and consequently, have found that if the resin film 3 laminated on the surface of the rubber stopper body 2 has the specified surface property, i.e. a surface roughness represented by an average roughness Ra on the central line of the surface in a range of at most 0.05 µm, measured according to JIS B0601-1982, and a kinematic friction coefficient of at most 0.2, measured according to JIS K7218-1986, a very high sealing property and slidable property can be realized. From the standpoint of a resin film having both the sanitary property and chemical stability required in the field of the sealing stopper for a syringe and a prefilled syringe of the present invention, the PTFE film and UHMWPE film are most suitable. In particular, the PTFE film prepared by a casting method using the specified raw materials or the UHMWPE film prepared by the inflation shaping method or extrusion shaping method is most suitable because of the capability of adjusting the surface roughness to the scope of the present invention. The present invention is based on this finding. Thus, a high sealing property and slidable property (low kinematic friction resistance) can be obtained to improve the quality holding property of medicaments and make easy medical operations.

FIG. 1(a), (b) and (c) are schematic views for illustrating a sealing stopper for a syringe (which will hereinafter be referred to as "sealing stopper") and prefilled syringe according to the present invention. As shown in FIG. 1(a), the sealing stopper 1 has the resin film 3 consisting of PTFE or UHMWPE laminated on the surface of the rubber stopper body 2. Since the prefilled syringe of the present invention is also used as a container for an injection liquid medicament, it is required that a resin film laminated on a rubber surface not only has physical sealing property and slidable property, but also it is hardly subject to adsorbing or elusion even if contacted with a medicament for a long time and not harmful to the human body.

The reason why PTFE is particularly selected and used from various fluoro resins in the present invention is that PTFE has such a stable property that dissolving or swelling does not appear in substantially all medicaments, PTFE has such an excellent heat resistance of organic materials that at about 327° C. (corresponding to the melting point), it becomes only transparent gel-like and does not show melt flow property, and the continuous application temperature is very high, i.e. about 260° C., a PTFE film has a surface excellent in hydrophobic property, lipophobic property and non-sticky property and PTFE has an excellent slidable property such as represented by a smaller kinematic friction coefficient as shown in Table 1 than that of other plastics.

According to these advantages, physical properties and chemical properties required for a surface laminating film of a sealing stopper for a syringe can be satisfied because of being resistant to a sterilizing processing at a high temperature in a formulation process, being free from adsorption or elusion even if contacted with a medicament filled inside for a long time and chemically stable and having such a high slidable property that a sealing stopper can smoothly be thrusted in a syringe during administration of a medicament.

Furthermore, the reason why UHMWPE is used as another laminating film consists in that various polyethylenes, in general, have chemical stability and high chemical resistance, very high melt viscosity and good thermal stability. UHMWPE having a molecular weight of at least one hundred million, in particular, is excellent in wear resistance, shock resistance and self lubricating property, has such a small friction coefficient similar to PTFE that it can preferably be used as a coating resin and is so excellent in radiation resistance that it can be applied to sterilization by radiation.

In Table 1 are shown kinematic friction coefficients as a coefficient for showing the degree of sliding (slidable property) of PTFE and UHMWPE for comparison with other resins, measured by JIS K7218-1986.

TABLE 1

| Resin | Kinematic Friction Coefficient (kg/cm$^2$ · m/sec) |
| --- | --- |
| Polytetrafluoroethylene (PTFE) | 0.2 |
| Ultrahigh Molecular Weight Polyethylene (UHMWPE) | 0.2 |
| Nylon 66 | 0.4 |
| Polyoxymethylene | 0.4 |

In the present invention, a PTFE film or UHMWPE film having an average roughness Ra on the central line of the surface in a range of at most 0.05 µm according to JIS B0601-1982 is used, and the film capable of satisfying this characteristic value shows a very smooth surface and allows sufficiently to display elasticity of a rubber stopper.

PTFE or UHMWPE of the present invention can be produced by any one of production processes capable of giving the specified surface roughness and kinematic friction coefficient, but since the PTFE film meets with the problem of pinholes when it is subjected to slicing or skiving as described above, it is particularly preferable to employ a casting method capable of providing excellent surface properties so as to realize the above described surface roughness.

Figure 2:
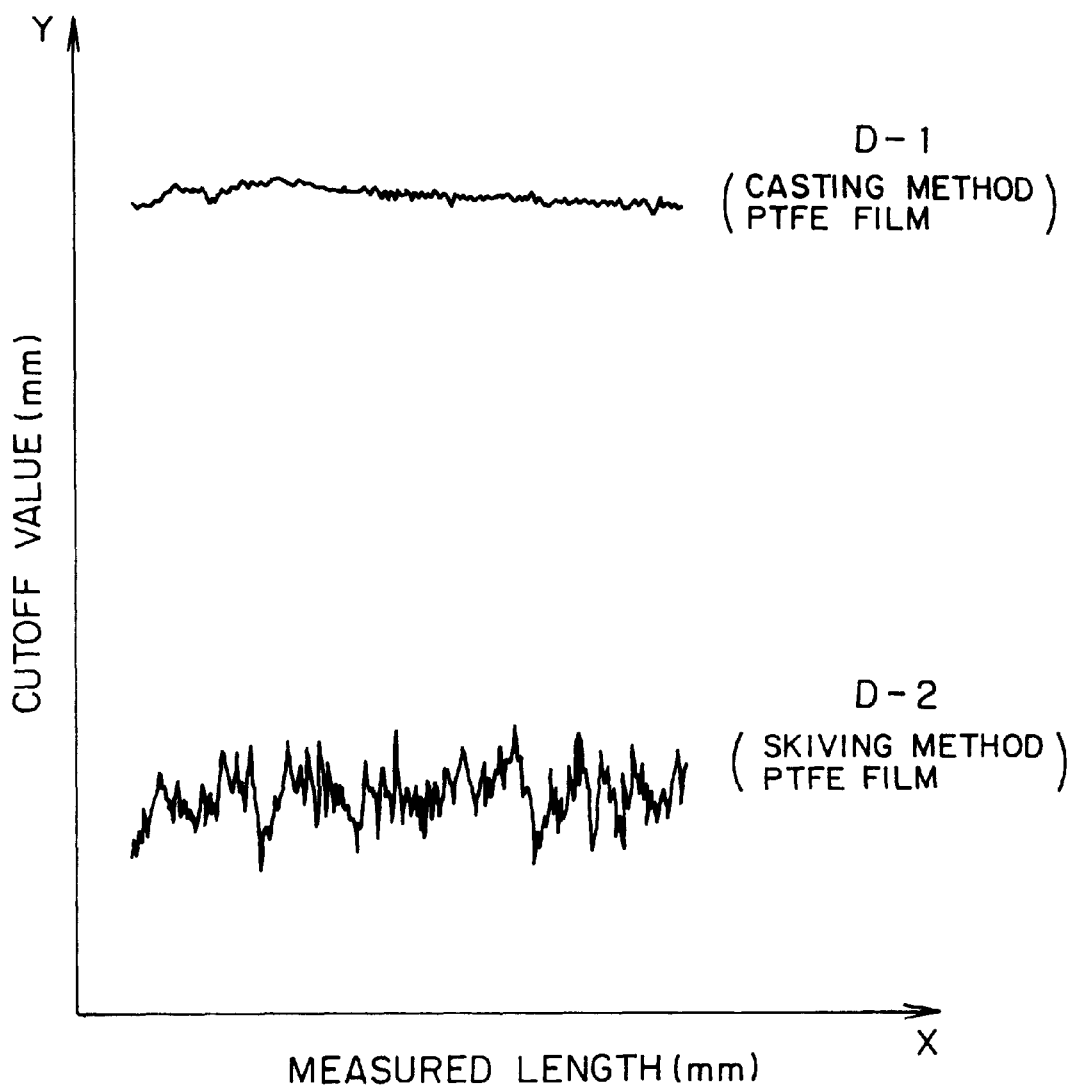
FIG. 2 is a chart with a multiplication of about 60000 times, showing measured data of surface roughness of a PTFE film obtained by a casting method used in Example of the present invention and a PTFE film obtained by a skiving method used in Comparative Example, for comparison.

FIG. 2 is a chart showing measured data of surface roughness of a PTFE film (D-1) obtained by a casting method used in Reference Example 1 and a PTFE film (D-2) obtained by a skiving method used in Reference Example 2 for comparison, respectively measured by JIS B0601-1982. The, x-direction shows a measured length (unit mm), y-direction shows a cut-off value (unit mm) and the maximum height (Rmax) is a height difference between the maximum value and minimun value, represented with a multiplication of about 60,000 times. As is evident from FIG. 2, the surface of film D-1 is much smoother than that of D-2.

UHMWPE having a very high melting point can be formed into a thin film by a method comprising heating under pressure and skiving a primary molding in an analogous manner to PTFE as described above before obtaining a sheet or film or sintering it into a sheet. Since the skiving method has the above described problem, however, it is particularly preferable to employ an extrusion method or an inflation forming method comprising closing one end of a UHMWPE film formed in a tubular form and blowing compressed air into the tubular form from the other end thereof to inflate it. Thus, the specified surface roughness on the central line of the surface in a range of at most 0.05 µm according to the present invention is realized in the similar manner to D-1 except omitting the measured chart.

As the thickness of a film to be laminated on a rubber stopper body is thinner, the rubber elasticity can more effectively be utilized and the sealing property is better, but handling of the film is difficult during producing and lamination working of the laminated stopper. Thus, the thickness of the PTFE film or UHMWPE film according to the present invention is generally about 0.001 mm to 0.1 mm, preferably 0.001 to 0.05 mm, more preferably 0.005 to 0.03 mm. In the real manufacturing, the void ratio is low in the case of a thickness range of 0.01 to 0.05 mm, the proportion defective being decreased. Production of a sealing stopper with a laminated film thickness of at most 0.001 mm is difficult and this is a critical limit in the lamination working of a rubber stopper body. On the other hand, a thickness exceeding 1 mm is not preferable because of not obtaining high sealing property.

Production of a PTFE film by a casting method will specifically be illustrated. A PTFE suspension is prepared by the use of a suitable dispersing agent, the suspension having such a grain diameter that a stable suspended state can be maintained, i.e. a maximum grain diameter of 0.01 to 1.0 µm, preferably at most 0.5 µm, and a solid concentration of about 35 to 60%. A more preferred concentration is about 40 to 50%. As a solvent and dispersing agent, there can be used commonly used ones. As a dispersant, for example, there is used a nonionic surfactant such as Nissan Nonion HS 208 (Commercial Name, manufactured by Nippon Yushi Co., Ltd.). As a solvent, for example, water can be used. In Table 2 are shown examples of compositions of the suspensions without limiting the present invention.

TABLE 2

| | Weight (g)/ Volume (1) | Resin Concentration (weight %) | Density of Suspension |
|---|---|---|---|
| PTFE | 900 | 60 | 1.50 |
| Resin | 693 | 50 | 1.39 |
| | 601 | 45 | 1.34 |
| | 515 | 40 | 1.29 |
| | 436 | 35 | 1.24 |
| Surfactant[1] | 1 weight % | | |
| Solvent[2] | 1 liter (total) | | |

(note)
[1]Nissan Nonion HS 208 (Commercial Name, manufactured by Nippon Yushi Co., Ltd.)
[2]water The suspension is poured onto a high heat resistance, rust proofing belt, for example, stainless steel belt, heated in a heating furnace of closed type at a temperature of higher than the melting point of PTFE (327° C.) to evaporate water content and then subjected to sintering working for 4 to 6 hours to form a thin film. Since the feature of this method consists in directly preparing a thin film without a step of preparing a cylindrical primary work as in other methods, there can be obtained a thin film free from pinholes or surface scratches due to the above described skiving working method. Furthermore, a very fine PTFE with a maximum grain diameter of at most 1.0 µm is herein used, thus resulting in a film product with a true specific gravity of approximately 2.14 to 2.20, which scarcely has pinholes even as a result of visual observation or pinhole investigation and exhibits very small surface roughness, i.e. excellent smoothness.

A rubber used for the sealing rubber stopper of the present invention is not particularly limited, but is exemplified by synthetic rubbers such as isoprene rubbers, butadiene rubbers, styrene butadiene rubbers, ethylene propyrene rubbers, isoprene-isobutylene rubbers, nitrile rubbers, etc. and natural rubbers. The rubber used as a predominant component can be blended with additives such as fillers, cross-linking agents, etc. For the sealing stopper for a prefilled syringe according to the present invention, however, it is preferable to select a material excellent in sanitary property as well as in gaseous permeability resistance so as to stably store a liquid medicament for a long time, e.g. 3 years in a container (injection cylinder). A compounding example of such a rubber formulation is shown in the following Table 3. When a PTFE film having a high softening point is laminated, Compounding Examples 1 and 2 each using a high vulcanization temperature are suitable, and when a UHMWPE film having a melting point of 135° C. is laminated, Compounding Examples 3 and 4 are suitable. In the present invention, the shape of the rubber stopper body and production process thereof are not particularly limited.

TABLE 3

| | Compounding | | | |
|---|---|---|---|---|
| Composition | Example 1 | 2 | 3 | 4 |
| Butyl Rubber[1] | 100 | | | |
| Chlorinated Butyl Rubber[2] | | 100 | | |
| Isobutylene-Isoprene-Divinylbenzene Terpolymer Partially Cross-linked Butyl Rubber[3] | | | 100 | |
| Acrylonitrile-Butadiene Rubber[4] | | | | 100 |
| Wet Process Hydrous Silica[5] | 35 | 30 | 30 | 20 |
| Dipentamethylene Thiuram Tetrasulfide[6] | 2.5 | | | |
| Zinc Di-n-dibutylthiocarbamate[7] | 1.5 | | | |
| Active Zinc Oxide[8] | 5 | 4 | 1.5 | |
| Stearic Acid[9] | 1.5 | 3 | | |
| Magnesium Oxide[10] | | | 1.5 | |
| 2-Di-n-butylamino-4,6-dimercapto-s-triazine[11] | | | 1.5 | |
| 1,1-Bis(t-butylperoxy)-3,3,5-tri-methylcyclohexane[12] | | | 2 | 8 |
| Total (weight part) | 145.5 | 140.0 | 133.5 | 128 |
| Vulcanization Conditions | | | | |
| Temperature (° C.) | 175 | 180 | 150 | 155 |
| Time (min) | 10 | 10 | 10 | 10 |

(Note):
[1]manufactured by Exxon Chemical Co., Esso Butyl # 365 (commercial name), bonded isoprene content: 1.5 mol %, Mooney viscosity: 43 to 51
[2]manufactured by Exxon Chemical Co., Esso Butyl HT 1066 (commercial name), bonded chlorine content: 1.3 wt %, Mooney viscosity: 34 to 40
[3]manufactured by Bayer AG, Bayer Butyl XL-10000 (commercial name)
[4]manufactured by Nippon Zeon Co., Nipol DN 102 (commercial name), bonded acrylonitrile content: 42 wt %, Mooney viscosity: 60
[5]manufactured by Nippon Silica Kogyo Co., Nipseal ER (commercial name), pH: 7.5 to 9.0 (5% aqueous solution)
[6]manufactured by Kawaguchi Kagaku Kogyo Co., Accel TRA (commercial name), MP: at least 120° C.
[7]manufactured by Kawaguchi Kagaku Kogyo Co., Accel BZ (commercial name)
[8]manufactured by Seido Kagaku Kogyo Co., Active Zinc White AZO (commercial name), ZnO 93 to 96%
[9]manufactured by Kao Co., Lunack S# 30, (commercial name)
[10]manufactured by Kyowa Kagaku Kogyo Co., Kyowa Mag # 150 (commercial name), specific surface area: 130 to 170 mg
[11]manufactured by Sankyo Kasei Co., Jisnet DB (commercial name) MP: at least 137° C.
[12]manufactured by Nippon Yushi Co., Perhexa 3M-40 (commercial name), molecular weight: 302, one minute half-life temperature: 149° C.

Figure 3:
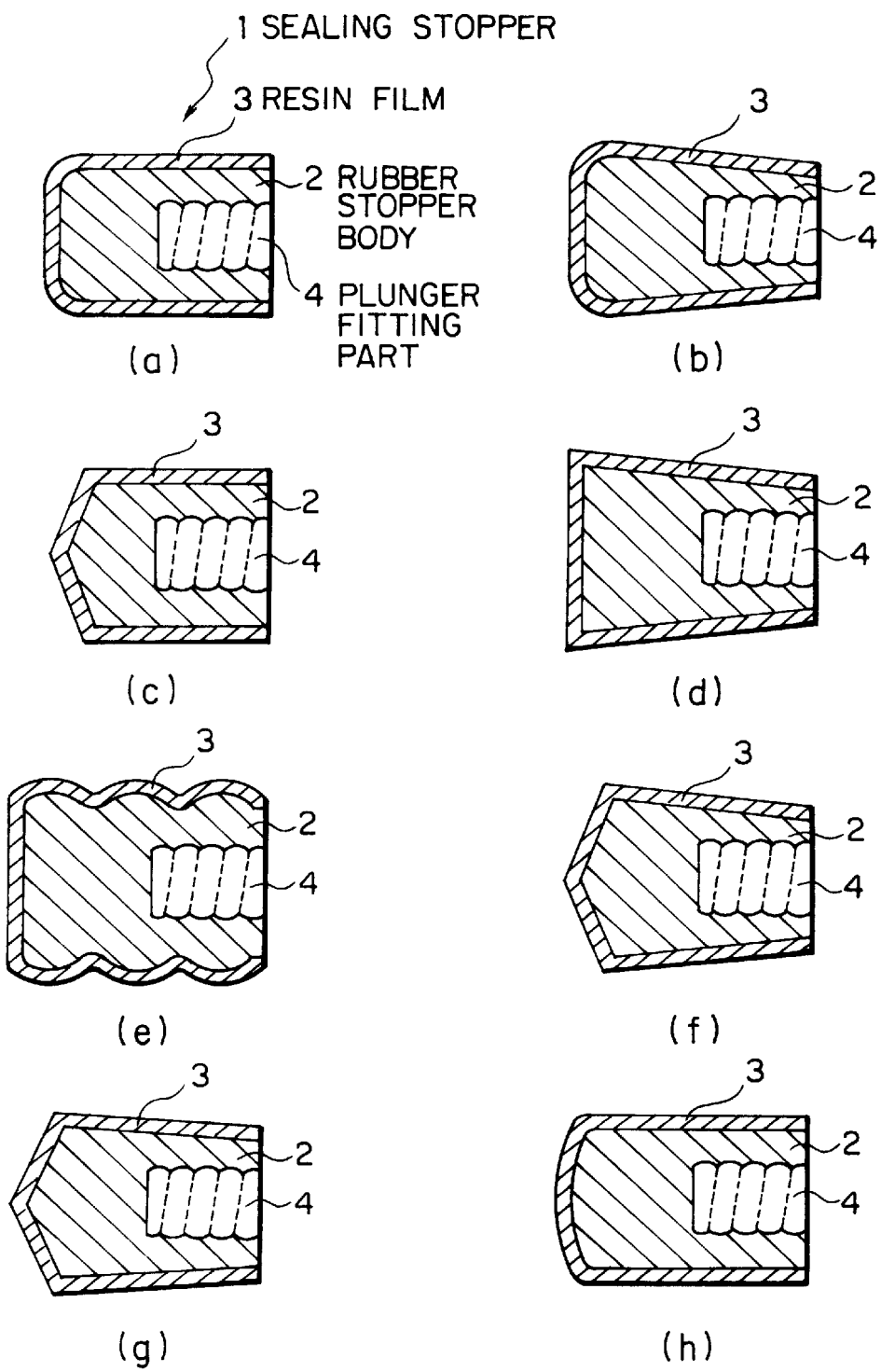
FIG. 3(a) to (h) are cross-sectional views of various shapes of the sealing stoppers according to the present invention.

Lamination of a surface of a rubber stopper with a PTFE film or UHMWPE film according to the present invention can be carried out by a known technique, for example, comprising subjecting one side of a film to a chemical etching treatment, sputtering treatment or corona discharge treatment, arranging the film in a metallic mold for shaping with a rubber compound as a base material of a sealing stopper body and then vulcanizing, or bonding and shaping in a predetermined shape. FIG. 3 shows various shapes, in cross section, of sealing stoppers of the present invention without limiting the same. Even if a syringe has a complicated structure, for example, in which a plurality of annular projections are formed on a slidable area of an inner wall of the syringe, the advantages of the present invention can of course be obtained. An area to be laminated includes a part in contact with an inner wall of a syringe or a part in contact with a medicament and is not intended to be limited thereto.

Since the sealing stopper of the present invention has a very high slidable property, even if the sealing stopper is designed in such a size that its compressibility, i.e. sealing property becomes higher by enlarging a difference between an inner diameter of an injection cylinder and an outer diameter of the sealing stopper, as shown in Examples hereinafter described, sufficient slidable property can be obtained.

The sealing stopper of the present invention can be applied to not only plastic injection cylinders, but also glass injection cylinders. However, since glass surfaces generally have larger roughness than plastic surfaces, the sealing stopper of the present invention can be applied to the plastic injection cylinders with better sealing property and sliding property.

The prefilled syringe of the present invention includes any one of the syringes of prefilled type using the sealing stopper for syringes according to the present invention hereinbefore illustrated. There is no limitation concerning materials or shapes of injection cylinders and other parts, for example, caps at front ends thereof, plunger rods provided at the back end of the sealing stopper, etc. For example, as a material for an injection cylinder (including two-component vessel), there are generally used plastics from the standpoint of the above described surface roughness, such as cyclic olefin resins, cyclic olefin-ethylene copolymer, polyethylene terephthalate resins, polystyrene resins, etc. In particular, cyclic olefin resins and cyclic olefin-ethylene copolymer are preferably used because of having higher transparency and heat resistance and having no chemical interaction with medicaments.

FIG. 1(c) shows a state of fitting a sealing stopper 1 to an injection cylinder 5. In the case of a prefilled syringe, a medicament is previously charged in the injection cylinder 5 serving also as a vessel for storage of an injection agent 7. The sealing stopper 1 is thrusted therein to close the injection cylinder to obtain a product. 6 designates a cap for closing an injection needle-fitted opening at the end of the injection cylinder 5. The syringe of this type includes the so-called kit articles. Since the storage period of a medicament generally extends to a long period of time, i.e. three years, in particular, sealing property, chemical resistance and chemical stability are required for the sealing stopper and during use, moreover, higher slidability and operativeness must be provided for emergency. The article of the present invention can satisfy all the requirements.

The present invention will now be illustrated in detail by the following Examples and Comparative Examples without limiting the same.

Reference Example 1

Production of PTFE Film (D-1) by Casting Method 6.01 kg of PTFE fine powder (Hostaflon TF 1760 -commercial name-, manufactured by Hoechst AG, maximum grain diameter: less than 1 $\mu$m, mean grain diameter: 0.1 $\mu$m) was added to 10 liters of Nissan Nonion HS 208 (nonionic surfactant) diluted with distilled water to 6% and adequately suspended and dispersed by means of a homogenizer to obtain 16.01 kg of a 45 weight % PTFE suspension. The suspension was coated onto a cleaned and polished stainless steel plate to give a coating thickness of 10 $\mu$m (generally, 5–20 $\mu$m), dried for 1.5 minutes by an infrared lamp and heated at 360–380° C. for about 10 minutes to evaporate the surfactant. After repeating this procedure four times (generally, 1–8 times), the suspension was sintered in a thickness of about 40 $\mu$m (0.04 mm) (generally, 10–60 $\mu$m). After the last sintering, the resulting layer was quenched with water and stripped from the metal plate to obtain a clear PTFE casting film (D-1). The number of the procedures was increased or decreased and thus, a film with a desired thickness could be obtained.

Reference Example 2

Production of PTFE Film (D-2) by Skiving Method

For comparison, a PTFE film was produced by the skiving method of the prior art, as described in the column of Prior Art (D-2). The same PTFE fine powder as that of Reference Example 1 was uniformly charged in a metallic mold having a diameter of 250 mm and height of 2000 mm and being of a polished stainless steel sheet, while passing through a stainless steel sieve of 10 mesh. The fine powder was gradually compressed to 300 kg/cm$^2$ at normal temperature and maintained for 25 minutes to obtain a preformed product, which was heated to 370° C. at a rate of 10° C./min in an electric furnace and maintained at this temperature until the whole material was uniformly sintered. The sintered product was then cooled to room temperature at a temperature lowering rate of 15° C./min to obtain a sintered article. The thus obtained sintered round rod (300 mm diameter×500 mm h) was subjected to skiving working, thus obtaining a PTFE film with a thickness of about 40 $\mu$m or a desired thickness.

The surface roughness of thus resulting D-1 and D-2 films and an ETFE film (D-3) obtained by an extrusion method as Reference Example 3 was measured by the following measurement method using a surface roughness and shape measurement device (Surface 550A -commercial name-, manufactured by Tokyo Seimitsu Co.) at a magnification of 60000, a cutoff value of 0.5 mm and a measured length of 4.0 mm, thus obtaining results as shown in Table 4. This measurement was carried out as to only the film, not after laminated, since the measurement of the laminated film was impossible from the structure of the measurement device.

Measurement Method of Roughness Depth on Film Surface

Measurement of the surface roughness was carried out according to JIS B0601-1982 using the surface roughness and shape measurement device of needle touch type (Surface 550A). While the needle part of the measurement device was applied to a surface of a sample and moved within a predetermined range, an average roughness (Ra) on the center line, maximum height (Rmax) and ten point average roughness (Rz) were measured to obtain a measured chart, from which Ra, Rmax and Rz were read. The measurement was carried out six times as to each sample and arithmetical average values of Ra, Rmax and Rz were obtained excluding the maximum value. Ra and Rz values represented the roughness depths of the film surface by numeral as an arithmetical average of all the roughness depth profiles from the center line.

As to each of the foregoing Samples D-1 to D-3, a film of 20 μm thick was prepared and subjected to measurement of the kinematic friction factor of the surface according to the following measurement method. Measured results and properties of the each film are shown in Table 4.

Measurement Method of Kinematic Friction Factor

The kinematic friction factor is a factor representative of a degree of sliding (slidability) of a film. According to JIS K7218-1986, the kinematic friction factor of a surface of a sample was measured using a friction and abrasion tester of Matsubara type (manufactured by Toyo Poldwin Co.) under test conditions of workpiece: SUS, load: 5 kgf–50 kgf (same load for 30 minutes every 5 kgf), speed: 12 m/min, time: 168 hours. Calculation of the kinematic friction factor was carried out by the following formula:

Kinematic Friction Factor (kg/cm$^2$·m/sec)

=kinematic friction force at vertical load of 15 kgf/load 15 kgf

Overall Light Percent Transmission and Haze

The overall light percent transmission and haze were measured according to JIS K7105-1981, "Test Method of Optical Properties of Plastics" using a device for measuring light transmission of integrated globe type. The haze means a ratio of scattered light to a quantity of transmitted light through a sample. The light percent transmission is a ratio of the overall light transmission and diffusion transmission to the quantity of the overall projected light.

10 minutes, and the whole body of the rubber stopper was laminated with PTFE or ETFE film to prepare a sealing stopper with a cross-sectional shape as shown in FIG. 3(a). The size of the sealing stopper was allowed to correspond to that of an injection cylinder used in each test described hereinafter.

Measurement of Sliding Resistance Value

Injection cylinders each having a volume of 5 ml and 100 ml, made of plastic (polypropylene), and sealing stoppers having sizes shown in Table 5, corresponding to these injection cylinders were prepared and each of the sealing stoppers was thrusted and set into the injection cylinder. The sealing stopper was slowly thrusted therein in such a manner that the end of the sealing stopper reached a position for defining a specified volume, thus preparing a sample injection cylinder. Then, a commercially available disposable injection needle having a determined size was firmly inserted into the end of the sample injection cylinder. Using a commercially available syringe fitted with an injection needle, on the other hand, distilled water with the specified volume of the injection cylinder was charged in the end of the sample injection cylinder, during which care was taken so that air was not allowed to enter therein. The end of the injection cylinder was directed downwards, inserted in a metallic jig and the sealing stopper was thrusted into the end side at a rate of 100 mm/sec by a compression test disk of spherical seat type of a pressure senser-fitted measurement device [Autograph AG-1KND -commercial name- manufac-

TABLE 4

| | | Reference Example 1 | Reference Example 2 | Reference Example 3 | Reference Example 4 |
|---|---|---|---|---|---|
| Film No. | | D-1 | D-2 | D-3 | D-4 |
| Resin: | Production | PTFE: | PTFE: | ETFE: | UHMWPE: |
| | Process | Casting Method | Skiving Method | Extrusion Method | Inflation Method |
| Central Line Average Roughness: Ra | | 0.036 μm | 0.136 μm | 0.03 μm | 0.032 μm |
| Maximum Height: Rmax | | 0.910 μm | 0.212 μm | 0.87 μm | 0.89 μm |
| Ten Point Average Roughness: Rz | | 0.396 μm | 1.290 μm | 0.23 μm | 0.30 μm |
| Kinematic Friction Factor | | 0.07 kg/cm$^2$ · m/sec | 0.10 kg/cm$^2$ · m/sec | 0.38 kg/cm$^2$ · m/sec | 0.20 kg/cm$^2$ · m/sec |
| Tensile Strength | Length Direction | 3.5 kg/mm$^2$ | 4.2 kg/mm$^2$ | 124 kg/mm$^2$ | 45,000 kg/mm$^2$ |
| | Width Direction | 3.5 kg/mm$^2$ | 2.0 kg/mm$^2$ | 118 kg/mm$^2$ | 43,500 kg/mm$^2$ |
| Elongation | Length Direction | 360% | 450% | 1057% | 350% |
| | Width Direction | 340% | 460% | 1273% | 340% |
| Overall Light Percent Transmission | | 92% | 88% | 99% | 55% |
| Haze | | 33% | 82% | 1% | 38% |
| Heat Shrinkage | Length Direction | 0.8% | 1.5% | 0.5% | 20% |
| (100° C.) | Width Direction | 0.7% | −1.2% | 0.4% | 25% |
| Heat Shrinkage | Length Direction | 1.8% | 2.9% | 1.4% | MP 135° C., |
| (200° C.) | Width Direction | 1.7% | −1.8% | 1.2% | impossible to measure |

Example 1 and Comparative Examples 1 and 2

In the following Example and Comparative Examples, a rubber sheet having an excellent gas permeability resistance of Compounding Example 2 in Table 3 was used. According to the compounding formulation, the mixture was kneaded using an open roll, aged for 24 hours and heated to obtain an unvulcanized rubber sheet. The resulting rubber sheet and D-1, D-2 and D-3 films with a thickness of 20 μm, obtained in the foregoing Reference Examples, were placed on a metallic mold for shaping, corresponding to a cross-sectional shape of a stopper shown in FIG. 3(a), pressing at a mold-fastening pressure of 150 kg/cm$^2$ depending on the vulcanization conditions of at 150 to 180° C., vulcanized for tured by Shimazu Seisakujo KK], during which a sliding resistance value was measured. The maximum value was read from the thus resulting sliding measured chart to define this as the sliding resistance value. In general, there was a tendency such that a value at the start of sliding, i.e. static friction resistance value Ffs was smaller than a value during sliding (kinematic friction resistance value) Ffd. The results are shown in Table 5, from which it is evident that in Comparative Example 3 in which FTFE was laminated, the slidability is too low to measure the sliding resistance value and it is difficult to set in the injection cylinder.

TABLE 5

|  |  | | Comparative | |
|---|---|---|---|---|
| Injection Cylinder Volume (ml) | Diameter of Sealing Stopper (mm) | Example 1 PTFE Coated Sealing Stopper by Casting Method | Example 2 PTFE Coated Sealing Stopper by Skiving Method | 3 ETFE Coated Seal-Stopper by Extrusion Method |
| 5 | 12.89 | 21.1 N* | 20.4 N | not measurable |
| 100 | 32.58 | 68.8 N | 59.3 N | not measurable |

(Note): *Newton (1 N = 9.8 kg)

Test for Estimation of Sealing Property for Long time
(Alternative Test for Estimation of Presence or Absence of Invasion of Microorganisms)

Using sealing stoppers of Example 1 and Comparative Examples 2 and 3 each having a size corresponding to an injection cylinder with a volume of 5 ml, the following procedure was carried out.

A plastic injection cylinder (volume 5 ml) having a cross-sectional shape shown in FIG. 1(c) was washed and dried, followed by sealing the end thereof by a rubber cap. Water with a predetermined volume was then poured therein and each of the above described sealing stoppers was slowly inserted into the opening part. In the case of Comparative Example 2, the sealing stopper was forcedly thrusted therein. The whole weight (initial weight) of the sample cylinder was precisely weighed and then subjected to storage under an accelerating condition of a temperature of 40° C. and relative humidity of 75% for at least 6 months. During each one month, each sample injection cylinder was taken and the surface thereof was dried for 30 minutes in a desiccator, followed by precisely weighing each sample (at least five measurement points). The resulting data of weight change was treated in a statistical manner to calculate a regression function, and a numerical value corresponding to three years is extrapolated in the time term to estimate and assess the sealing property for a long time after formulation of a medicament. In order to correspond to the real formulation, seventy samples were respectively prepared and investigated as to both plunger fitted- and plunger-free sealing stoppers.

A reduction curve Y for the time term X of each sample, $Y = -K + \alpha \ln X$, obtained by the above described statistical procedure can be represented in Example 1, as follows:
When fitting a plunger: $Y = -1.896 + 1.087 \times \ln X$ . . . (a)
When not fitting a plunger: $Y = -4.200 + 1.594 \times \ln X$ . . . (b)
When into the time term X of the above described regression function formulas (a) and (b) are extrapolated two years (17,520 hours) and three years (26,280 hours) to estimate weight reductions after two years and three years under a normal state of water for injection in each sample, the weight reductions are 5.27 mg after two years and 5.71 mg after three years in the case of (a). The reduction ratios when the initial weight is 100% are 0.11% in two years and 0.11% in three years. Similarly, the estimated values of the reduction and reduction ratio in the case of (b) are 6.31 mg and 0.12% in two years and 6.96 mg and 0.13% in three years.

The similar procedure to that of Example 1 was also carried out as to Comparative Example 1 (D-2) and Comparative Example 2 (D-3) to obtain reduction curves, and reductions and reduction ratios after two years and three years, obtained by extrapolation of the reduction curves. The results are shown in Table 6.

As shown in Table 6, the sealing property of the film (ETFE) of D-3 is more excellent, but the sealing stopper of Comparative Example 2 having this film laminated is inferior in slidability between the film and inner wall of the injection cylinder because of a much higher sliding resistance so that it cannot be put to practical use. Even when using the same PTFE film, Example 1, in which the film by the casting method was laminated, is more excellent in slidable property and sealing property than Comparative Example 1, in which the film by the skiving method was laminated.

TABLE 6

| Example | Laminated Resin (Reference Example): Production Process | Plunger | Reduction Curve (Regression Function) $Y = -\alpha + K \cdot \ln X$ | Reduction and Reduction Ratio After 2 Years | Reduction and Reduction Ratio After 3 Years |
|---|---|---|---|---|---|
| Example 1 | PTFE (D-1): Casting Method | yes | $Y = -1.896 + 1.087 \ln X$ | 5.27 mg 0.11% | 5.71 mg 0.11% |
|  |  | no | $Y = -4.200 + 1.594 \ln X$ | 6.31 mg 0.12% | 6.96 mg 0.13% |
| Comparative Example 1 | PTFE (D-2): Skiving Method | yes | $Y = -6.357 + 3.518 \ln X$ | 16.84 mg 0.32% | 17.79 mg 0.34% |
|  |  | no | $Y = -6.676 + 3.617 \ln X$ | 17.17 mg 0.32% | 18.64 mg 0.35% |
| Comparative Example 2 | ETFE (D-3) Extrusion Method | yes | $Y = -7.379 + 2.683 \ln X$ | 10.31 mg 0.19% | 11.40 mg 0.22% |
|  |  | no | $Y = -7.214 + 2.658 \ln X$ | 10.31 mg 0.19% | 11.39 mg 0.21% |

Example 2

This Example was carried out as to a sealing stopper having an UHMWPE film laminated within the scope of the present invention, prepared by the extrusion method, and another sealing stopper having an UHMWPE film laminated (D-4) in an analogous manner to Example 1, Comparative Example 1 or 2, thus obtaining similar good results to Example 1.

From the foregoing tests, it could be confirmed that the present invention was very excellent in sealing property as well as slidable property.

Results of various tests effected as a sealing stopper for a syringe will be shown using the sealing stopper, as a typical example, of the type of Example 1 using the film of D-1.

Test for Liquid Sealing Property (a) Dynamic Loading Conditions

Compressing Test according to Notification No. 442 of the Ministry of Health and Welfare, Standard of Device for Medical Treatment, "Standard of Disposal Injection Cylinder", Dec. 28, 1970, and British Standard.

Ten samples of clean plastic injection cylinders each having a specified volume were prepared, the end (lure part) of the injection cylinder being sealed by applying a rubber cap thereto. An aqueous Methylene Blue solution of 0.1 weight/volume % concentration in only a determined volume was poured in the injection cylinder. A rubber sealing stopper having a resin film laminated on the surface thereof according to the present invention or a comparative rubber stopper was slowly thrusted from the flange part of the injection cylinder and while turning up the head of the cylinder, the rubber cap was taken off at the lure part. A plastic plunger was screwed in a threaded part at the opening side of the sealing stopper and slowly pushed up upwards in such a manner that the liquid in the cylinder was not leaked, thus pushing out air in the end part of the cylinder. A rubber cap was again applied to the lure part and mounted on a measurement device for pressure test. After a pressure defined for medical treatment as shown in Table 7 was added for 10 seconds, the injection cylinder was taken off from the measurement device and an interface between the sealing stopper and injection cylinder was observed while magnifying ten times to confirm whether there was a leakage of the above described blue aqueous Methylene Blue solution through the interface part or not (Compressing Test ①). The measured results are shown in Table 8, from which it is apparent that the sealing stopper of the present invention exhibits no leakage in any size of injection cylinders. In addition, Table 8 shows simultaneously the compressibility and sliding resistance of sealing stoppers, which teaches that even a sealing stopper having a larger compressibility (higher sealing property) has a higher sliding property.

When a further larger pressure was added to investigate presence or absence of leakage in addition to the above described defined Compressing Test (Compressing Test ②), there was found no leakage as shown in Table 8.

TABLE 7

| Application | Volume for Injection Cylinder | Pressure (10 sec.) |
| --- | --- | --- |
| General Medical Treatment | less than 3 ml | 4.0 kg/cm$^2$ |
| | at least 3 ml less than 10 ml | 3.5 kg/cm$^2$ |
| | at least 10 ml less than 20 ml | 3.0 kg/cm$^2$ |
| | at least 20 ml less than 30 ml | 2.5 kg/cm$^2$ |
| | at least 30 ml | 2.0 kg/cm$^2$ |
| Very Small Amount | less than 2 ml | 5.0 kg/cm$^2$ |
| | at least 2 ml | 4.0 kg/cm$^2$ |
| Insulin | long | 5.0 kg/cm$^2$ |
| | short | 4.0 kg/cm$^2$ |

TABLE 8

| | Injection | | | | Compressing Test ① | | Compressing Test ② | |
| --- | --- | --- | --- | --- | --- | --- | --- | --- |
| Injection Cylinder Volume (min) | Cylinder Inner Diameter (mm) | Sealing Stopper Outer Diameter (mm) | Compressibility (%) | Sliding Resistance (N) | Pressure (kg/cm$^2$) | Test Results (Observation) | Pressure (kg/cm$^2$) | Test Results (Observation) |
| 1 | 6.8 | 7.1 | 4.8 | 11.4 | 4.0 | no leakage | 6.9 | no leakage |
| 3 | 8.7 | 9.1 | 4.5 | 20.7 | 3.5 | no leakage | 5.9 | no leakage |
| 5 | 12.4 | 12.9 | 3.8 | 21.1 | 3.5 | no leakage | 3.7 | no leakage |
| 10 | 15.0 | 15.5 | 3.3 | 16.3 | 3.0 | no leakage | 3.5 | no leakage |
| 20 | 20.0 | 21.0 | 2.1 | 13.5 | 2.5 | no leakage | 3.5 | no leakage |
| 50 | 29.5 | 30.2 | 2.4 | 11.9 | 2.0 | no leakage | 2.6 | no leakage |
| 100 | 32.2 | 32.9 | 1.2 | 68.1 | 2.0 | no leakage | 2.5 | no leakage |

[note]
Compressibility = [(Stopper Outer Diameter − Cylinder Inner Diameter)/Stopper Outer Diameter] × 100%

Test for Liquid Sealing Property (b) Accelerated Conditions

Plastic injection cylinders having various volumes ten by ten and sealing stoppers having sizes corresponding thereto and end caps ten by ten were prepared. In a plastic injection cylinder whose end was covered with a cap was poured a 1% aqueous Methylene Blue solution of a determined volume and then the sealing stopper of the present invention and the stopper for comparison were slowly inserted respectively from the opening part of the injection cylinder. After passage of at least six months under accelerating conditions of a temperature of 40° C. and a relative humidity of 75%, it was confirmed by visual observation whether there was leakage of the above described aqueous Methylene Blue solution at the interface between the plastic injection cylinder and sealing stopper. This method was carried out as a test method for proving that in the case of formulation of a liquid injection agent through a sterile formulation step, there was no leakage of the liquid medicament nor invasion of a liquid material from the outside.

Test for Liquid Sealing Property (c) Severer Conditions

Each of samples prepared in an analogous manner to the above described accelerating test was subjected to confirmation of the presence or absence of leakage of the above described aqueous Methylene Blue solution at the interface between the plastic injection cylinder and the sealing stopper by heating at 121° C. for 30 minutes using an autoclave. This method is a method for estimating a sealing property in a formulation step, which comprises adding a stress similar to a formulation step of a part of a liquid injection agent, sterilized after the formulation. The results of the foregoing (b) and (c) are shown in Table 9.

Gas Sealing Property Test (Invasion of Steam: Test according to "Moisture Permeability Test of US Pharmacopoeia", 22nd Edition)

Injection Cylinders each having a volume of 1 to 100 ml (ten by ten) as shown in Table 8 were precisely weighed, a drying agent was charged in the injection cylinder, maintained standing, in such a manner that the thickness (height) be 13 mm, and the sealing stopper was fixed at a scale of the injection cylinder, representing a specfified volume. As the drying agent, there was preferably used calcium chloride passing through a 4-mesh sieve, dried at 110° C. for 1 hour and then cooled in a desiccator. After precisely weighing the weight (Ti) of each sample, the sample was preserved at a temperature of 20° C. and a humidity of 75% RH, and after passage of 14 days, the weight (Tf) was precisely weighed again. An increment of weight for a period of 14 days (Tf−Ti) was sought. On the other hand, for control, the initial weight (Ci) and the weight (Cf) after passage of 14 days were precisely weighed concerning dried glass beads-charged samples instead of the calcium chloride to obtain the increment of weight (Cf−Ci) for control for a period of 14 days. When the volume of the injection cylinder is V, the moisture permeability can be given by the following formula. The results are shown in Table 9.

Moisture Permeability=(100/14 V)[(Tf−Ti)−(Cf−Ci)]

TABLE 9

| Injection Cylinder Volume (ml) | Liquid Sealing Property Test[1] Results | Liquid Sealing Property Test[2] Results | Gas Sealing Property Test[3] Results (mg/day · 1) |
| --- | --- | --- | --- |
| 1 | no leakage of MB[4] | no leakage of MB | −1 |
| 3 | no leakage of MB | no leakage of MB | −1 |
| 5 | no leakage of MB | no leakage of MB | 2 |
| 10 | no leakage of MB | no leakage of MB | 22 |
| 20 | no leakage of MB | no leakage of MB | 25 |
| 50 | no leakage of MB | no leakage of MB | 30 |
| 100 | no leakage of MB | no leakage of MB | 2.8 |

(Note)
[1] accelerating condition: 40° C., 75% RH, 6 months
[2] severer condition: 121° C., 1 hour
[3] moisture permeability test: 20° C., 75% RH, 14 days
[4] MB: Methylene Blue In the moisture permeability test, a sealing property to gas (steam) at a setting part of a plastic injection cylinder and sealing stopper is estimated, but this test can be considered to be an alternative test for estimating the possibility of invasion of microorganisms. The results of the moisture permeability within a range of −1 to 30 mg/day, liter according to the present invention, as shown in Table 9, teach very high sealing property.

Substantially similar good results could be obtained in an estimation test as to the sealing stopper having UHMWPE laminated in Example 2.

Advantages of the Invention

As illustrated above, according to the present invention, there can be obtained a sealing stopper for a syringe, which has more improved slidability as well as sealing property, to such a degree that even if the compressibility of a rubber stopper is rendered higher, smooth sliding can be obtained, by laminating a PTFE film or UHMWPE film with a very excellent surface property. In particular, the sealing property in a formulation step (high temperature or pressure condition) as well as the sealing property during storage for a long time are higher. Moreover, during use, administration of an injection medicament can be carried out in easy and rapid manner because of the higher sliding property, so that requirements in the real medical scenes may be satisfied. The above described advantages can similarly be obtained in the case of the prefilled syringe according to the present invention.

What is claimed is:

1. A sealing stopper for a syringe, comprising a rubber body laminated with a tetrafluoroethylene resin film or ultra-high molecular weight polyethylene film having an average roughness Ra on the central line of a surface of said resin film or said poluethylene film in a range of at most 0.05 μm and a kinematic friction coefficient of at most 0.2.

2. A sealing stopper for a syringe, as claimed in claim 1, wherein the tetrafluoroethylene resin film is prepared by a casting-shaping method comprising using, as a raw material, a suspension containing tetrafluoroethylene resin powder having a grain diameter of at most 0.01 to 1.0 μm, a dispersing agent and a solvent.

3. The sealing stopper for a syringe, as claimed in claim 1, wherein said ultra-high molecular weight polyethylene film is prepared by an inflation shaping method or an extrusion shaping method.

4. A prefilled syringe, comprising an injection cylinder or two-component cylinder for enclosing or sealing a medicament, the medicament being enclosed or sealed by a sealing stopper for a syringe having a rubber body laminated with a tetrafluoroethylene resin film or ultrahigh molecular weight polyethylene film having an average roughness Ra on the central line of a surface of said resin film or said polyethylene film in a range of at most 0.05 μm and a kinematic friction coefficient of at most 0.2.

* * * * *